United States Patent [19]

Tahbaz

[11] 4,292,323

[45] Sep. 29, 1981

[54] PHENYL-1,2,3,4-TETRAHYDROCARBAZOLES AND USE THEREOF

[75] Inventor: Pirouz Tahbaz, Cedar Grove, N.J.

[73] Assignee: Schering Corporation, Kenilworth, N.J.

[21] Appl. No.: 136,015

[22] Filed: Mar. 31, 1980

[51] Int. Cl.$^3$ .................... C07D 209/88; A61K 31/40
[52] U.S. Cl. ..................................... 424/274; 260/315
[58] Field of Search ........................ 260/315; 424/274

[56] References Cited

U.S. PATENT DOCUMENTS 3,959,309  5/1976  Mooradian ........................ 260/315

OTHER PUBLICATIONS

Green et al., *Chem Abstracts*, vol. 45 (1951), col. 10236d.

*Primary Examiner*—Henry R. Jiles
*Assistant Examiner*—R. W. Ramsuer
*Attorney, Agent, or Firm*—Carver C. Joyner; Bruce M. Eisen; Mary S. King

[57] ABSTRACT

This application relates to phenyl-substituted 1,2,3,4-tetrahydrocarbazoles and to their use as anti-depressant agents useful in the treatment of mental depression of either endogenous or reactive nature.

10 Claims, No Drawings

PHENYL-1,2,3,4-TETRAHYDROCARBAZOLES AND USE THEREOF

This invention relates to certain phenyl-substituted 1,2,3,4-tetrahydrocarbazoles, the pharmaceutical compositions and formulations thereof, to the novel processes and intermediates for making such compounds, and to their use as anti-depressant agents useful in the treatment of mental depression of either endogenous or reactive nature.

In one of its composition of matter aspects, this invention relates to phenyl-1,2,3,4-tetrahydrocarbazoles of the formula

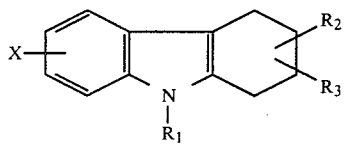

wherein

X is hydrogen, halogeno, nitro, amino, lower alkyl, hydroxy, lower alkoxy or $CF_3$, $R_1$ is hydrogen, lower alkyl, amido or aminoalkyl, $R_3$ is phenyl, or X-substituted phenyl, $R_2$ is hydrogen, cyano, amido, aminoalkyl, COOR with R being hydrogen or lower alkyl, with the proviso that $R_2$ and $R_3$ must both be located on the same carbon atom.

As used herein the term "lower" as it modifies such radicals as alkyl, alkoxy and the like is meant to include those radicals containing from 1-6 carbon atoms, including both the straight and branched manifestations thereof including such preferred radicals as methyl, ethyl, methoxy and the like.

The term "halogeno" includes all four members of this series with chloro, fluoro and bromo being preferred. The term amino includes not only the radical $NH_2$, but also those $-NR_4R_5$ radicals wherein $R_4$ and $R_5$ are hydrogen or lower alkyl. Similarly "amido" includes those radicals of the partial structure $-CONR_4R_5$, and the term "aminoalkyl" includes the $-(CH_2)_nNR_4R_5$ radicals wherein (n is one to six carbon atoms. As stated $R_2$ and $R_3$ are both located on the same carbon atom. Thus such radicals may be located at any of the 1-, 2-, 3- or 4-positions of the 1,2,3,4-tetrahydrocarbazole nucleus although it is preferred that the $R_2$ and $R_3$ radicals be attached to the 3-position carbon atom.

The preparation of the compounds of this invention is effected utilizing standard and well-known techniques. In general, the compounds of this invention (I) may be prepared by the condensation of an appropriately X-substituted phenyl hydrazine (II) with an appropriately substituted cyclohexanone using the standard Fisher-Indole synthesis reaction conditions.

In essence the reaction may be depicted by the following reaction scheme:

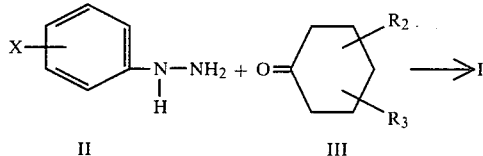

wherein X, $R_2$ and $R_3$ are as previously defined.

In effecting this condensation the reactants II and III are contacted together in an acidic medium, at elevated temperatures, for about ½ to 24 hours. Acids which may be utilized as cyclizing agents are inorganic acids such as hydrochloric and or hydrobromic acid, mineral acids such as sulfuric acid or phosphoric acids and organic acids such as acetic and methanesulfonic acid as well as Lewis acids such as boron trifluoride. The acidic agent should be present in at least one mole excess per mole of the phenylhydrazine. The reaction is conveniently carried out by heating the reactants in acetic acid or in ethanolic hydrochloric acid at reflux temperature for about one hour. The reaction proceeds via the phenylhydrazone precursor which can be isolated, although the use of excess acid will effect cyclization in situ to the desired tetrahydrocarbazole. The necessary $R_2R_3$-cyclohexanous reactants belong to a well-known and generally available group of chemicals. In those few instances wherein any particular cyclohexanone (III) is not known or available, then such reactants may be prepared by standard and conventional techniques well known in the art. Similarly, the necessary phenylhydrazine (II) reactants also belong to a well known class of chemicals and are generally available. In those instances wherein a particular reactant is not available then such reactant can be prepared by standard and well known methods.

Although reaction scheme A depicts the general method for preparing 1,2,3,4-tetrahydrocarbazoles, there are a few instances wherein it is more efficient (i.e., the phenylhydrazine cannot bear substituents which interfere with, or will not survive the reaction conditions of the Fischer indole synthesis and such substituents are introduced subsequent to the cyclization procedure as described hereinbelow) to prepare 1,2,3,4-tetrahydrocarbazoles which will serve as reactive intermediates for other compounds of this invention. In those instances wherein $R_1$ is other than hydrogen it is preferred to first synthesize a 1,2,3,4-tetrahydrocarbazole (hereinafter also referred to as tetrahydrocarbazole) having hydrogen at its 9-position (i.e., $R_1$ is hydrogen) which compound can be utilized to prepare compounds where $R_1$ is other than hydrogen. In those instances wherein $R_1$ is aminoalkyl then such compounds are prepared by standard and conventional N-alkylation procedures such as by reacting a (9-H compound with a reactive aminoalkyl halide in a suitable solvent in the presence of a strong base for about ½ to 8 hours. Preferably the reaction is carried out in dimethylformamide in the presence of sodium hydride at 75° C. to 85° C. for about two hours.

In those instances wherein $R_1$ is an amido radical then such compounds are prepared by standard and conventional N-acylation procedures such as by reacting a 9-H compound with an isocyanate bearing either a protective chlorosulfonyl moiety or the $R_4R_5$ lower alkyl radicals.

Preferably, the 9-H compound is reacted with chlorosulfonylisocyanate at room temperature in ether as a solvent, to product at

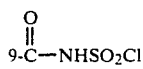

which chlorosulfonylamide when hydrolyzed with an alkali metal hydroxide (preferably KOH) in aqueous acetone at room temperature yield the desired amide. In those instances wherein $R_1$ is lower alkyl then such radical may be attached to the phenylhydrazine reactant or else they may be produced from 9-H, 1,2,3,4-tetrahydrocarbazoles by standard alkylating procedures.

Similarly, in those instances wherein $R_2$ is other than hydrogen then the necessary phenylcyclohexanones should not bear substituents which will interfere with or will not survive the reaction conditions of the Fischer indole synthesis. In those instances wherein $R_2$ is cyano than such radical-containing 1,2,3,4-tetrahydrocarbazole may be prepared from a phenylcyclohexanone (III) bearing a cyano group. However, when $R_2$ is COOH then that radical is prepared by the transformation of the cyano group to a COOH group. Generally such transformation is effected by hydrolysis preferably by heating the compound in a high boiling solvent such as ethylene glycol in the presence of an alkali metal hydroxide. The so-formed carboxy-containing 1,2,3,4-tetrahydrocarbazole may then be esterified by standard and conventional techniques such as by reaction with an alcohol in an acid at elevated temperature. The preparation of the aminoalkyl radicals may be effected by chemical reduction of a cyano radical using lithium aluminum hydride in tetrahydrofuran (THF) and the resulting intermediate is decomposed with dilute hydrochloric acid.

In those instances wherein X is hydroxy, then such compounds are prepared by treatment of the corresponding lower alkoxy along with a Lewis acid, preferably boron trifluoride, according to the standard and well-known techniques.

Having described in general terms the procedures by which the compounds of this invention may be prepared, the following examples will typify the specific techniques for obtaining the desired final products, although by no means are the inventive concepts herein described limited to the examples.

EXAMPLE I 6 methoxy-3-phenyl-1,2,3,4-tetrahydrocarbazole

To a mixture containing p-methoxy-phenylhydrazine hydrochloride (50.0 g) and 4-phenylcyclohexanone (50.0 g) add 500 ml of acetic acid and with constant stirring heat the mixture for one hour at 80°–90° C. Cool the mixture, add 200 ml of water and filter and dry the resulting precipitate. The product is recrystallized with methanol/water (1:1), m.p. 114°–115° C.

By substituting the p-methoxyphenylhydrazine HCl with equivalent quantities of the HCl salt of the following
X-substituted phenylhydrazine,
4-methylphenylhydrazine.
4-nitrophenylhydrazine,
4-chlorophenylhydrazine,
4-ethoxyphenyl hydrazine, phenylhydrazine
3,4-dimethoxyphenyl hydrazine,
3-methoxyphenylhydrazine
and by substantially following the foregoing Fischer indole synthesis these are produced
8-ethyl-3-phenyl-1,2,3,4-tetrahydrocarbazole,
6-methyl-3-phenyl-1,2,3,4-tetrahydrocarbazole,
6-nitro-3-phenyl-1,2,3,4-tetrahydrocarbazole,
6-chloro-3-phenyl-1,2,3,4-tetrahydrocarbazole,
6-ethoxy-3-phenyl-1,2,3,4-tetrahydrocarbazole,
6,7-dimethoxy-3-phenyl-1,2,3,4-tetrahydrocarbazole,
5-methoxy-3-phenyl-1,2,3,4-tetrahydrocarbazole and-/or
7-methoxy-3-phenyl-1,2,3,4-tetrahydrocarbazole.

Similarly replacement of the 4-phenylcyclohexanone with equivalent quantities of the following X-phenyl-$R_2$-cyclohexanones
4-methoxyphenyl-4-cyano-cyclohexanone,
4-phenyl-4-cyano cyclohexanone,
4-carboxy-4-phenyl-cyclohexanone,
4-methylphenyl-4-cyano-cyclohexanone,
4-chlorophenyl-cyclohexanone,
4-fluorophenyl-cyclohexanone,
and by substantially following the procedure of the foregoing example these are produced
3-cyano-3-(4-methoxyphenyl)-1,2,3,4-tetrahydrocarbazole,
3-cyano-3-phenyl-1,2,3,4-tetrahydrocarbazole,
3-phenyl-3-carboxy-1,2,3,4-tetrahydrocarbazole,
3-cyano-3-(4-methylphenyl)-1,2,3,4-tetrahydrocarbazole,
3-(4-chlorophenyl)-1,2,3,4-tetrahydrocarbazole,
3-(4-fluorophenyl)-1,2,3,4-tetrahydrocarbazole.

Similarly, by utilizing those X-substituted-phenylhydrazines listed above with those X-substituted-4-phenylcyclohexanones listed above, and by substantially following the same procedure of this example the appropriately X-substituted-3-phenyl-1,2,3,4-tetrahydrocarbazoles are produced.

EXAMPLE II 6-methoxy-3-aminomethyl-3-phenyl-1,2,3,4 tetra-hydrocarbazole HCl To 6-methoxy-3-cyano-3-phenyl-1,2,3,4-tetrahydrocarbazole (1.0 g) in tetrahydrofuran (10 ml) is added lithium aluminum hydride (0.4 g) and the mixture is reflured for one hour, 0.1 ml of water is cautiously added, and the resulting mixture is filtered. The filtrate is evaporated to dryness, the residue dissolved in methylene chloride and then ethered. HCl is added to precipitate the desired compound.

EXAMPLE III 3-phenyl-9-carboxamido-1,2,3,4-tetrahydrocarbazole

Chlorosulfonyl isocyanate (2.8 g) in ether (10 ml) is slowly added to a cold solution (0°–10° C.) of 3-phenyl-6-methoxy-1,2,3,4-tetrahydrocarbazole (5.5 g) in ether (50 ml) and the resulting solution is stirred at room temperature for 2½ hours, and then evaporated to dryness at 1:7 mixture of water and acetone (80 ml) is added to the residue followed by the addition of 10% $NH_4OH$ (50 ml) and the mixture is stirred at room temperature for ½ hour. The solid obtained thereby is recrystallized with ethylacetate to yield the desired product.

EXAMPLE IV 6-methoxy-3-carboxy-3-phenyl-1,2,3,4-tetrahydrocarbazole

A mixture containing 6-methoxy-3-cyano-3-phenyl-1,2,3,4-tetrahydrocarbazole (48.0 g) potassium hydroxide (60.0 g) in ethylene glycol (300 ml) is heated at 170° C. for 16 hours and then cooled. To the cooled solution is added dilute HCl to bring the mixture to pH 8. The resulting precipitate is recrystallized with acetonitrile to give the desired compound.

EXAMPLE V 6-methoxy-3-phenyl-9-dimethylaminopropyl-1,2,3,4-tetrahydrocarbazole A mixture containing 6-methoxy-3-phenyl-1,2,3,4-tetrahydrocarbazole (5.5 g), 50% sodium hydride (1.0 g) in dimethylformamide (30 ml) is heated at 100° C. for 1½ hours, and then dimethylamino propyl chloride is added. The mixture is heated at 80° C. for 2 hours, then cooled and water (40 ml) is added. The solid which precipitates is recrystallized with methylene chloride:ether (1:1).

As stated above, the compounds of this invention (I) are anti-depressants useful in the treatment of mental depression of either endogenous or acute (i.e., reactive) nature.

The anti-depressant activity of the compounds of this invention may be ascertained by testing in standard biological test procedures (e.g., the rat muricide test). The testing is effected both in terms of their absolute activity and also by comparison against such well-known standards as amitryptyline and imipramine. On the basis of the standard testing procedures, either on an absolute basis or on a comparative basis, it is found that these compounds (I) exert their anti-depressant activity in the treatment of mental depression at dosage levels of about 0.5 to 6 MPK per day, preferably in 3-4 divided doses. Preferably the compounds of this invention are administered in amounts of 25-300 mg per day in 3-4 divided doses. In addition to the results of the foregoing test procedure, it is also found that the compounds of this invention will have, when compared to such standards as imipramine or amitryptyline, a relatively fast onset of action and will exert little or no antichlinergic side effects.

In their use as anti-depressants the compounds may be prepared into standard pharmaceutical formulations suitable for oral, rectal or parenteral administration by formulation techniques well known in the art, such as for example tablets, capsules, aqueous or oily suspensions or solutions, emulsions, powders, suppositories and the like. Suitable adjuvants such as calcium carbonate, starch, lactose, talc, magnesium sterate, gum acacia and the like are advantageously used.

Preferred compounds of this invention are those wherein $R_1$ is hydrogen, X is hydrogen or methoxy (preferably in the 6-position), $R_3$ is phenyl or halo or alkoxy substituted phenyl, and $R_2$ is hydrogen. Specifically preferred compounds are those wherein X is 6-$OCH_3$, $R_3$ is phenyl and $R_1$ and $R_2$ are hydrogen;

X is 6-chloro $R_1$ and $R_2$ are hydrogen and $R_3$ is p-fluorophenyl;

X is 6-methyl $R_1$ and $R_2$ are hydrogen and $R_3$ is phenyl;

and X is 6-cloro $R_1$ and $R_2$ are hydrogen and $R_3$ is p-methoxyphenyl.

I claim:

1. A 1,2,3,4-tetrahydrocarbazole of the formula

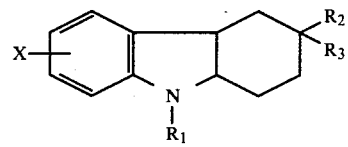

wherein X is methoxy, halo or methyl; $R_1$ and $R_2$ are hydrogen and $R_3$ is phenyl or halo or alkoxy substituted phenyl.

2. A compound of claim 1 wherein X is methoxy.

3. A compound of claim 3 wherein X is halogeno.

4. A compound of claim 1 wherein $R_3$ is phenyl.

5. A compound of claim 1 wherein $R_3$ is p-fluorophenyl.

6. A compound of claim 1 wherein X is 6-methoxy, $R_1$ and $R_2$ are hydrogen and $R_3$ is 3-phenyl, said compound being 6-methoxy-3-phenyl-1,2,3,4-tetrahydrocarbazole.

7. A compound of claim 1 wherein $R_1$ and $R_2$ are hydrogen, X is 6-chloro and $R_3$ is p-fluorophenyl.

8. A compound of claim 1 wherein $R_2$ and $R_1$ are hydrogen, X is 6-methyl and $R_3$ is phenyl.

9. A compound of claim 1 wherein $R_2$ and $R_1$ are hydrogen, X is 6-chloro and $R_3$ is p-methoxyphenyl.

10. A method for treating mental depression in warm blooded animals which comprises administering thereto a therapeutically effective quantity of a compound of claim 1.

* * * * *